(12) United States Patent
Feller et al.

(10) Patent No.: US 7,344,562 B2
(45) Date of Patent: Mar. 18, 2008

(54) AAA LOW PROFILE SUPPORT STRUCTURE

(75) Inventors: Frederick Feller, Coral Springs, FL (US); David C. Majercak, Stewartsville, NJ (US); Jin S. Park, Parsippany, NJ (US); Diana M. Sanchez, Bernardsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 289 days.

(21) Appl. No.: 11/188,498

(22) Filed: Jul. 25, 2005

(65) Prior Publication Data

US 2006/0025846 A1    Feb. 2, 2006

Related U.S. Application Data

(60) Provisional application No. 60/591,954, filed on Jul. 28, 2004.

(51) Int. Cl.
*A61F 2/06* (2006.01)
(52) U.S. Cl. ...................... 623/1.35; 623/1.13
(58) Field of Classification Search ............... 623/1.35, 623/1.16, 1.18, 1.13, 1.36, 1.23; *A61F 2/06*
See application file for complete search history.

(56) References Cited

U.S. PATENT DOCUMENTS

| | | | |
|---|---|---|---|
| 5,851,228 A * | 12/1998 | Pinheiro | 623/1.13 |
| 6,224,625 B1 | 5/2001 | Jayaraman | |
| 6,319,278 B1 | 11/2001 | Quinn | |
| 6,699,277 B1 | 3/2004 | Freidberg et al. | |
| 7,175,657 B2 * | 2/2007 | Khan et al. | 623/1.35 |
| 2001/0014823 A1 * | 8/2001 | Ressemann et al. | 623/1.13 |
| 2002/0072790 A1 | 6/2002 | McGuckin et al. | |
| 2003/0065380 A1 | 4/2003 | Kugler et al. | |
| 2003/0120338 A1 * | 6/2003 | Chobotov et al. | 623/1.36 |
| 2003/0125797 A1 * | 7/2003 | Chobotov et al. | 623/1.13 |
| 2003/0130720 A1 * | 7/2003 | DePalma et al. | 623/1.13 |
| 2003/0153969 A1 | 8/2003 | Dehdashtian et al. | |
| 2005/0113906 A9 * | 5/2005 | Bolduc et al. | 623/1.35 |

FOREIGN PATENT DOCUMENTS

| WO | WO 03/075799 A | 9/2003 |
|---|---|---|
| WO | WO 2004/105636 A | 12/2004 |

* cited by examiner

*Primary Examiner*—Brian E. Pellegrino
*Assistant Examiner*—Jason-Dennis Stewart

(57) ABSTRACT

An endoprosthesis for repairing and treating abdominal aortic aneurysms. The endoprosthesis features an anchoring and sealing component and low profile bifurcated legs. A biocompatible graft material is secured to at least the bifurcated legs in order to provide two endoleg fluid flow lumens or conduits. The bifurcated legs have staggered stent elements that nest to contribute to the low profile nature of the device and additional longitudinal struts between pair of the staggered stent elements to increase the longitudinal stiffness of the bifurcated legs while maintaining the patency of the lumen created thereby.

16 Claims, 5 Drawing Sheets

OPTION 1

OPTION 2

AAA LOW PROFILE SUPPORT STRUCTURE

CROSS REFERENCE TO RELATED APPLICATIONS

This application claims the benefit of prior U.S. Provisional Patent Application Ser. No. 60/591,954 filed Jul. 28, 2004.

BACKGROUND OF THE INVENTION

1. Field of the Invention

The present invention relates to abdominal aortic aneurysm devices, and more particularly to an abdominal aortic aneurysm device, wherein the bifurcated legs contribute to a low profile device by having longitudinal struts in the bifurcated legs that provide structural support to the device.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3 F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The market today is populated by devices approximately 20 F and greater requiring the need for a surgical cut-down approach utilizing catheters, guidewires and accessory devices which substantially eliminate the need for open surgical intervention. Although, the cut-down approach significantly reduces the acute complications that often accompany open surgical intervention, the ultimate goal and the market trend is to reduce delivery system profiles and to perform the procedure of delivering an endoprosthesis percutaneously, as by the Seldinger technique which eliminates the need for a cut-down procedure.

SUMMARY OF THE INVENTION

The present invention aims to overcome the disadvantages associated with larger endoprostheses as briefly described above.

In accordance with one aspect, the present invention is directed to an endoprosthesis. The endoprosthesis comprises a cranial section having a substantially tubular structure configured to anchor and seal the endoprosthesis within a vessel, a caudal section having at least two legs in fluid communication with the cranial section, the at least two legs each comprising a plurality of stent elements and a plurality of longitudinal struts in the space between the stent elements In some embodiments the longitudinal struts are directly connected to one or more of the stent elements, whereas in other embodiments the longitudinal struts are not directly connected to the stent elements. Graft material is attached to at least a portion of the cranial section and to the at least two legs thereby forming at least two fluid flow conduits.

The endoprosthesis of the present invention offers a number of advantages over existing devices. The endoprosthesis may be anchored and sealed supra or infra-renally. The stent elements comprising the bifurcated legs are staggered relative to one another so that they are nested during delivery, thereby reducing the overall profile of the device. In addition, the endoprosthesis of the present invention has better overall wear resistance due to the elimination of some stent elements. The endoprosthesis comprises longitudinal struts between the stent elements in the bifurcated legs. The longitudinal struts may be attached to one or more of the stent elements or may simply be positioned therebetween. The struts add longitudinal stiffness and columnar strength to the legs and may further comprise receptacles for attaching the endoleg material of the bifurcated legs thereto. The struts still further may comprise eyelets through which the graft material of the endoprosthesis may be stitched, sutured or otherwise attached to the strut. In one embodiment, the bifurcated legs are connected together along a longitudinally central portion for further enhancing the column stiffness and strength of the device. The connection between the legs may be temporary or permanent. The temporary connection may be made of biodegradeable sutures, for example, or other material as should be appreciated by the artisan.

BRIEF DESCRIPTION OF THE DRAWINGS

The foregoing and other features and advantages of the invention will be apparent from the following, more particular description of various embodiments of the invention, as illustrated in the accompanying drawings.

DETAILED DESCRIPTION OF THE PREFERRED EMBODIMENTS

The various embodiments of the invention described herein are directed to an endovascular graft which may be utilized as a component in a system for use in treating or repairing aneurysms. Systems for treating or repairing aneurysms such as abdominal aortic aneurysms and thoracic aortic aneurysms come in many forms. A typical system includes an anchoring and/or sealing component which is positioned in healthy tissue above the aneurysm and one or more grafts which are in fluid communication with the anchoring and/or sealing component and extend through the aneurysm and anchor in healthy tissue below the aneurysm. Essentially, the grafts are the components of the system that are utilized to establish a fluid flow path from one section of an artery to another section of the same or different artery, thereby bypassing the diseased portion of the artery. Current systems are typically delivered via catheter and deployed.

Figure 5A:
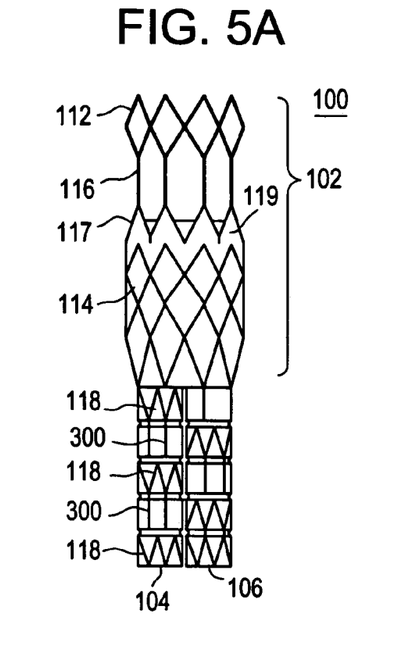
FIG. 5a is a diagrammatic representation of an alternate exemplary embodiment of an anchoring and sealing prosthesis with longitudinal struts connected to stent elements in accordance with the present invention.
Figure 5B:
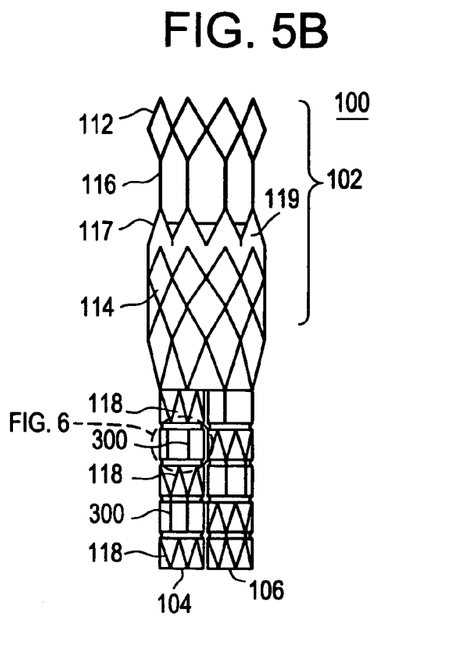
FIG. 5b is a diagrammatic representation of an alternate exemplary embodiment of an anchoring and sealing prosthesis with longitudinal struts not connected to stent elements in accordance with the present invention.
Figure 6:
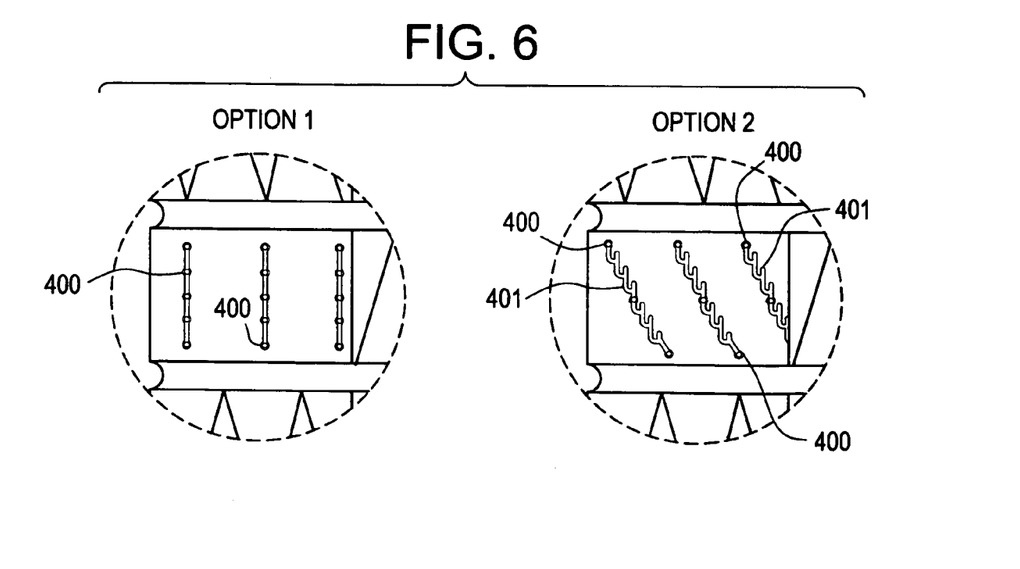
FIG. 6 is a detailed diagrammatic representation of various longitudinal supporting strut options.

The various embodiments of the invention described herein are directed to the anchor and sealing component of the endovascular graft or endoprosthesis. Generally, the endovascular graft of the present invention comprises a number of components that make up a modular system. Although the overall endovascular graft comprises a number of components, the challenges associated with these types of systems include profile, flexibility and accessibility. Loading an abdominal aortic aneurysm repair system or endovascular graft in a percutaneous delivery apparatus is not a simple task considering the amount of material that has to be delivered with such components. This is especially true of the anchoring and sealing component of the endoprosthesis. The anchoring and sealing component comprises a trunk section and a bifurcated section wherein the two legs comprising the bifurcated section are supported by metallic stent elements. There are a number of design features that may be built into the anchoring and sealing component of the endovascular graft in order to reduce its profile, namely, leaving spaces between the stent elements in each of the legs and staggering the position of the stent elements in each of the legs such that no two stent elements line up. In this manner, the two legs of the bifurcated section may be nested during delivery, thereby reducing the overall profile of the system. By staggering the stent elements of the bifurcated section, however, the column strength and lumen patency of each leg may be somewhat compromised, which in turn may lead to a cannulation problem during deployment. This problem may be overcome by adding the longitudinal support struts in the spacing between the stent elements. The longitudinal struts may be directly connected with one or more of the stent elements (FIG. 5a), or may simply be positioned between the various stent elements comprising the bifurcated legs (FIG. 5b). FIG. 6 shows in more detail various longitudinal strut options. Of course, the artisan will readily appreciate that additional columnar strength and support may be provided by stitching or otherwise connecting adjacent central portions of the bifurcated legs together. The stent elements are preferably zigzag patterned elements, or Z-stents, although the artisan will further readily appreciate that other stent element patterns may be used in the various embodiments described herein in order to provide desired columnar strength and lumen patency. Increasing the stiffness of the legs facilitates placement of the device.

Figure 1:
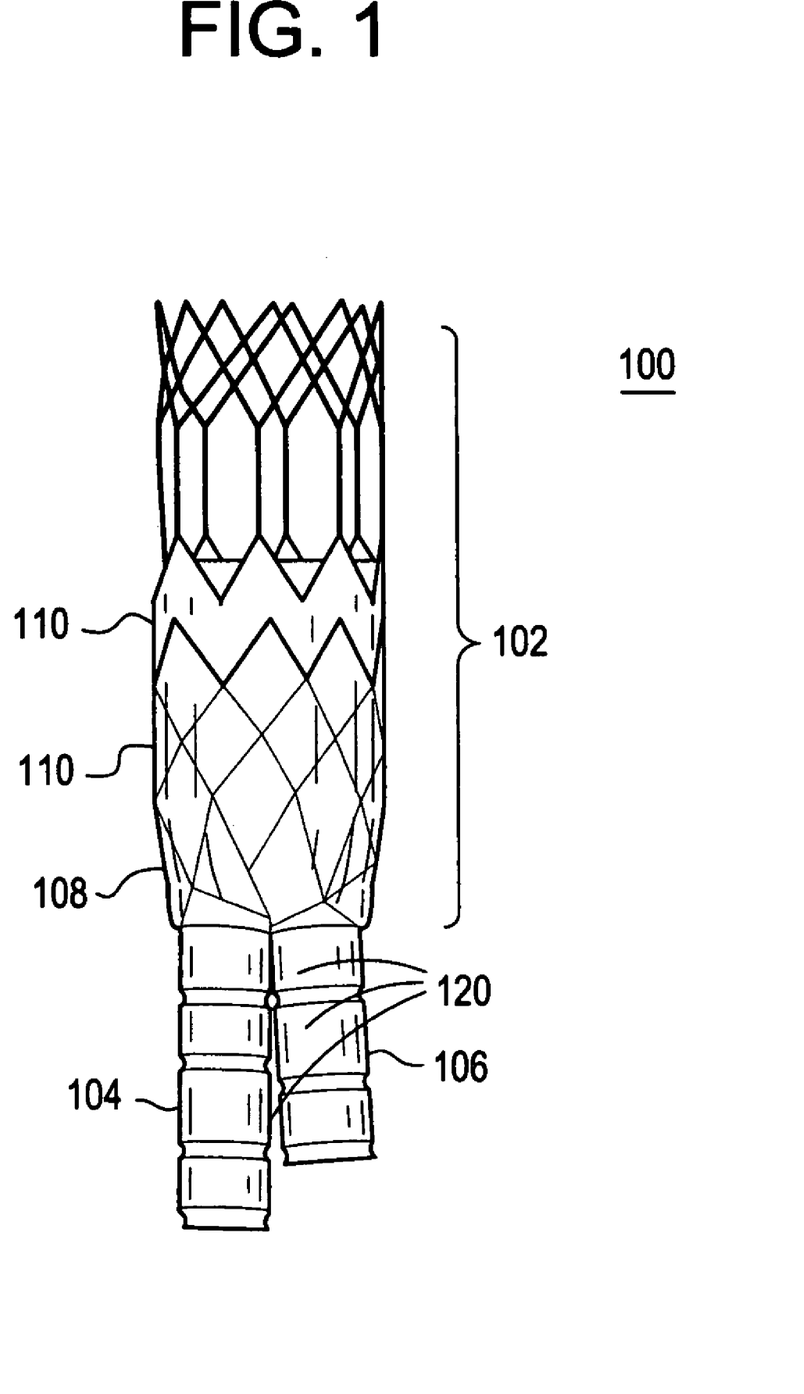
FIG. 1 is a diagrammatic representation of an exemplary anchoring and sealing prosthesis in accordance with the present invention.

Referring now to FIG. 1, there is illustrated an alternate embodiment of an anchoring and sealing component 100 in accordance with the present invention. As illustrated, the anchoring and sealing component 100 comprises a trunk section 102 and a bifurcated section, including two legs 104, 106. Graft material 108 is affixed to at least a portion of the trunk section 102 and all of the legs 104, 106. The graft material is attached to various portions of the underlying structure by sutures 110. As illustrated, the graft material 108 is affixed with a continuous stitch pattern on the end of the trunk section 102 and by single stitches elsewhere. It is important to note that any pattern may be utilized and other devices, such as staples, may be utilized to connect the graft material 108 to the underlying structure. The sutures 110 may comprise any suitable biocompatible material that is preferably highly durable and wear resistant.

Figure 2:
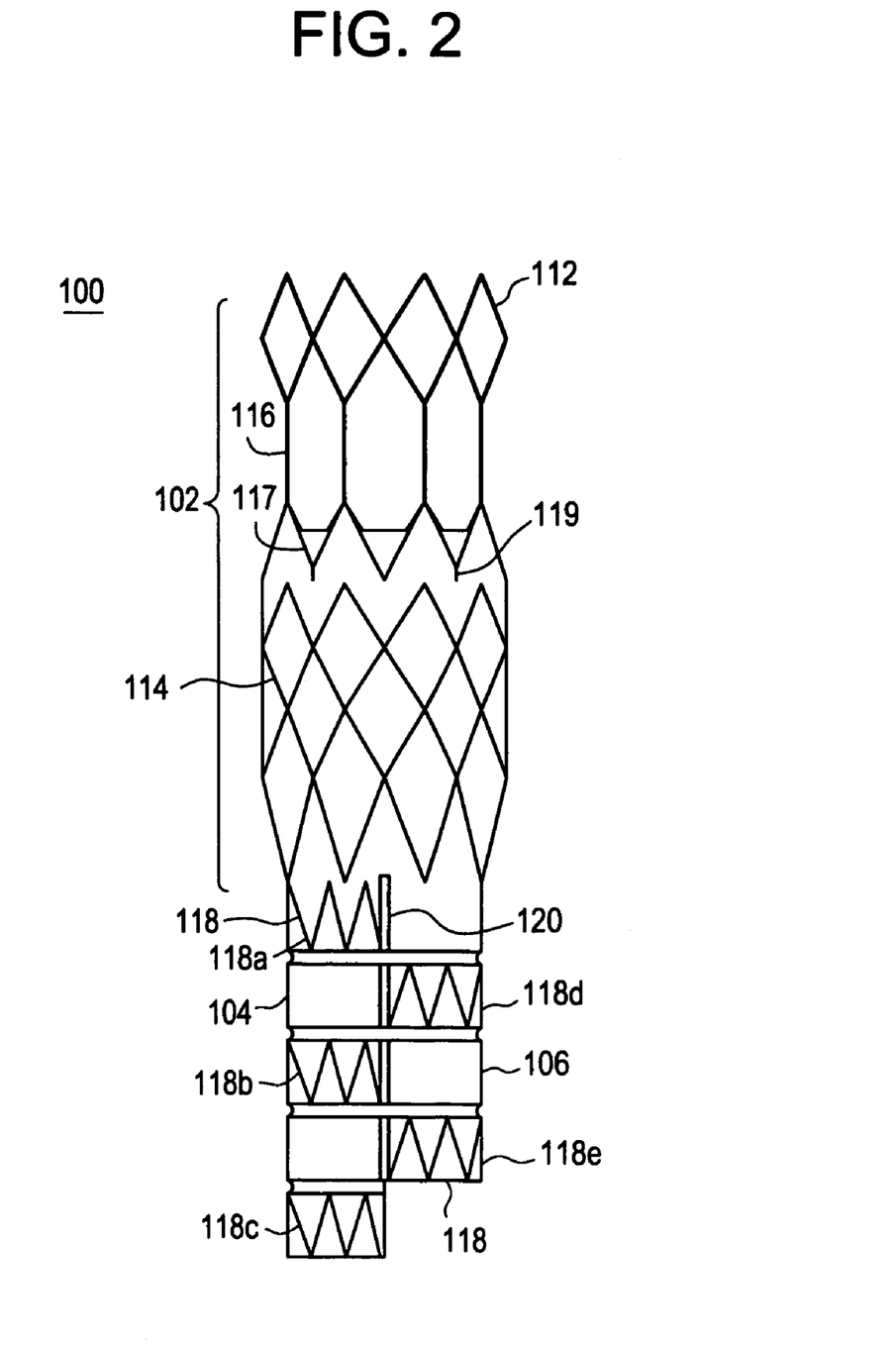
FIG. 2 is a diagrammatic representation of the exemplary anchoring and sealing prosthesis showing details of the underlying stent structure in accordance with the present invention.

The underlying structure of the trunk section 102, as illustrated in FIG. 2, comprises a substantially tubular stent structure or lattice comprising multiple stent sections. The stent or lattice structure comprises a single row of diamond elements 112 on one end, multiple rows of diamond elements 114 on the other end, a plurality of longitudinal struts 116 and a single, substantially zigzag shaped stent element 117. The plurality of longitudinal struts 116 are connected to apexes of the diamond elements 114. The single, substantially zigzag shaped stent element 117 comprises a number of barbs 119 protruding therefrom for anchoring. This embodiment may be utilized for anchoring and sealing in positions wherein there are branches off the main artery. For example, this embodiment may be utilized for supra-renal anchoring. Accordingly, the graft material 108 is only attached below the longitudinal struts 116 so that blood may flow into the renal arteries from the aorta. Infra-renal designs are also possible.

The underlying structure of the bifurcated section, as illustrated in FIG. 2, comprises a plurality of individual, substantially tubular stent elements 118. Each stent element 118 comprises a substantially zigzag pattern. As illustrated, leg 104 comprises three stent elements 118a, 118b, 118c and leg 106 comprises two stent elements 118d, 118e. Also illustrated is the fact that the stent elements do not line up and the legs are of two different lengths. As stated above, this design allows for nesting of the legs 104, 106 such that the profile of the device is reduced.

In order to compensate for any compromised columnar support or strength due to the spacing between the stent elements 118, the legs are connected at the bifurcation, i.e., along the adjacent central portions of the bifurcated legs, as illustrated in FIG. 1. The legs 104, 106 may be connected in any suitable manner. In the alternate embodiment shown in FIG. 1 the two legs 104, 106 are connected by suturing them together. The sutures 120 connect the graft material 108 on each leg 104, 106 together. The sutures may be non-biodegradable or biodegradable. Biodegradable sutures would dissolve over time thereby allowing the two legs to move independently. Other appropriate attachments devices could be used in lieu of the sutures, as should be readily apparent to the artisan.

Figure 3:
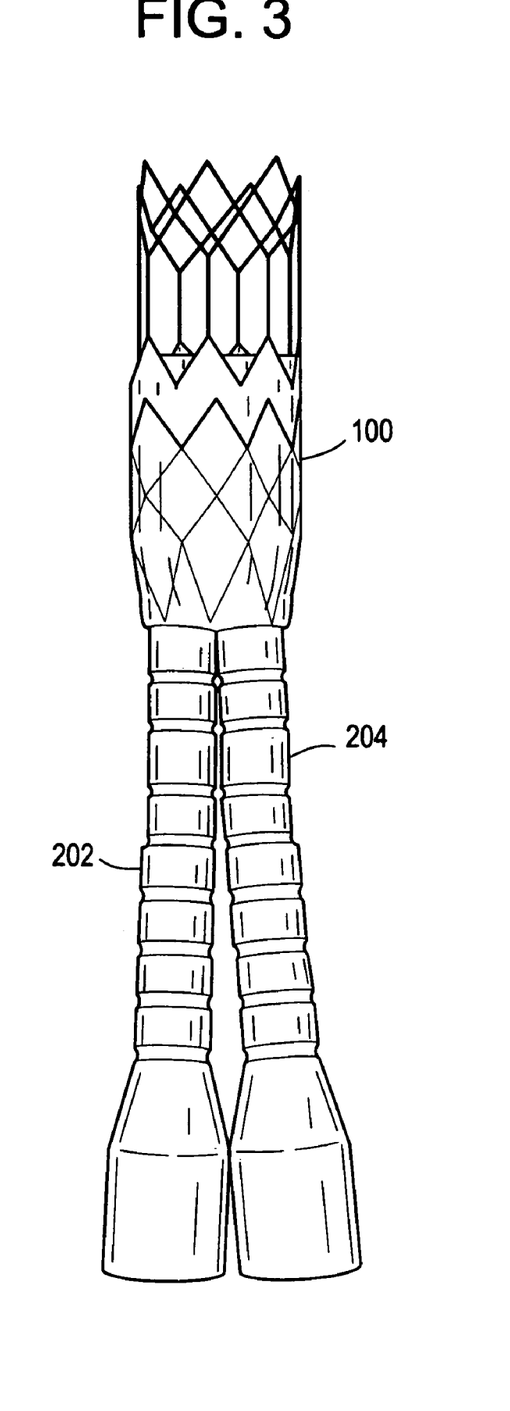
FIG. 3 is a diagrammatic representation of another exemplary abdominal aortic aneurysm repair device in accordance with the present invention.
Figure 4:
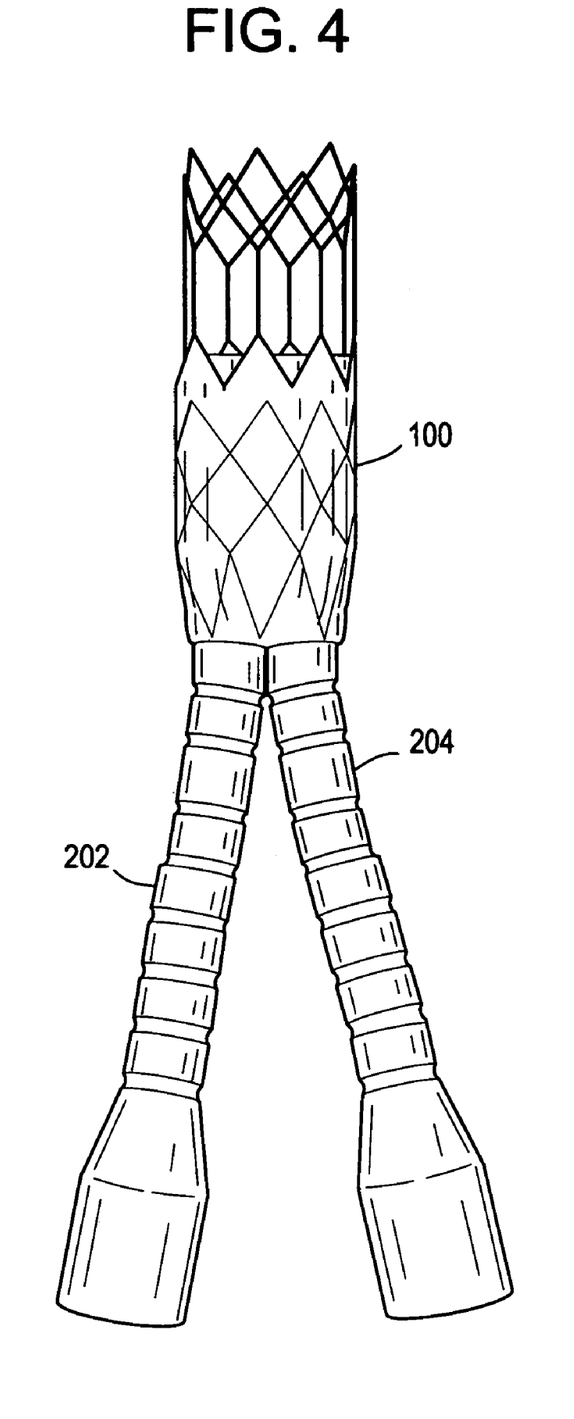
FIG. 4 is a diagrammatic representation of an exemplary abdominal aortic aneurysm repair device with the legs supported in accordance with the present invention.

FIGS. 3 and 4 illustrate the entire endovascular graft for repairing an abdominal aortic aneurysm. As may be seen, the entire endovascular graft comprises the anchoring and sealing component 100 and two grafts or endolegs 202 and 204. The grafts 202 and 204 each comprise a plurality of stent elements and graft material. The ends of the endolegs 202 and 204 may be flared for better anchoring and sealing in the downstream arteries. The flared section may be formed by flaring the last individual stent element. The endolegs 202, 204 are the bypass conduits through which the blood flows in the aneurysmal section of the artery. By eliminating the blood flow to the diseased section, the pressure is reduced and thus there is less of a chance of the aneurysm rupturing.

In other embodiments, a plurality of individual, longitudinally oriented strut elements may be positioned between the stent elements in each bifurcated leg. Referring to FIGS. 5a & 5b, there are illustrated such embodiments. As illustrated, the longitudinally oriented strut elements 300 are positioned between the stent elements 118 of each leg 104, 106. The longitudinal struts 300 add stiffness to each of the legs 104, 106. The longitudinal struts 300 may be attached to the stent elements 118 (FIG. 5a) or may be simply positioned therebetween (FIG. 5b). The struts 300 may also comprise eyelets 400 for attachment of the graft material during fabrication. For example, the struts may comprise eyelets 400 through which sutures, staples or other attachment devices are inserted for securing the graft material to the respective bifurcated legs via the struts, see FIG. 6. In addition, the struts 300 may comprise receptacles 401 that facilitate the anchoring of the endolegs thereto during deployment. For example, the receptacles 401 provide locations at which endoleg material, and primarily external suture knots 205 (FIG. 2), can attach.

Although the longitudinal struts 300 are shown in FIG. 6, Option 1, as primarily vertically oriented between stent elements, the struts 300 may be otherwise oriented. In this regard, even partial stent elements 118 could comprise the longitudinal struts similar to as shown in Option 2 of FIG. 6, for example. The artisan will appreciate that other partial stent configurations could as well comprise the longitudinal struts where desired. For example, in an alternate embodiment, the struts 300 are diagonally positioned between stent elements 118, see FIG. 6. Regardless of the orientation of the struts 300, each strut may comprise either or both of eyelets 400 and receptacles 401. Referring still to FIG. 6, and FIGS. 1-6 in general, the stent elements 118 and longitudinal struts 300 can be either internally or externally oriented relative to the graft material 108 of the device, except in those cases as in Option 2 of FIG. 6, where the receptacles 401 receive the external suture knots 205 of the endolegs 202, 204, whereby the longitudinal struts 300 are necessarily internal relative to the graft material 108.

The stent elements of the present invention may be formed from any number of suitable biocompatible materials, including metals, polymers and ceramics. In a preferred embodiment, the stent elements are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In some embodiments, each stent, comprised of the various stent elements and longitudinal struts, is fabricated from a single piece of alloy tubing. The tubing is laser cut, shape-set by placing the tubing on a mandrel, and heat-set to its desired expanded shape and size.

In various embodiments, the shape setting is performed in stages at appropriate temperatures as determined by the artisan. The shape setting may occur at five hundred degrees centigrade, for example. Where the shape setting occurs at five hundred degrees centigrade, for example, the stents are placed on sequentially larger mandrels and briefly heated to five hundred degrees centigrade. To minimize grain growth, the total time of exposure to a temperature of five hundred degrees centigrade can be limited. The stents are given their final shape set for four minutes at five hundred fifty degrees centigrade, and then blasted, as described in detail subsequently, before electropolishing. This heat treatment process provides for a stent that has a martensite to austenite transformation, which occurs over a relatively narrow temperature range, for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centigrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

The graft material or component, may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An endoprosthesis comprising:
    a cranial section having a substantially tubular structure configured to anchor and seal the endoprosthesis within a vessel;
    a caudal section having at least two legs in fluid communication with the cranial section, the at least two legs each comprising a plurality of stent elements; wherein, adjacent stent elements are alternately sequenced in a horizontal plane relative to one and a longitudinal strut positioned between each of the plurality of stent elements, each longitudinal strut is positioned between a pair of the plurality of stent elements; and
    graft material attached to at least a portion of the cranial section and to the at least two legs thereby forming at least two endoleg fluid flow conduits, each longitudinal strut comprising eyelets through which attachment devices are received for securing the graft material to the endoprosthesis and receptacles for receiving and securing a portion of the graft material comprising the two endoleg fluid flow conduits, the graft material comprises external sutures knots.

2. The endoprosthesis of claim 1, wherein each of the plurality of stent elements is comprised of a zigzag pattern.

3. The endoprosthesis of claim 1, wherein each of the plurality of stent elements is a Z-stent.

4. The endoprosthesis of claim 1, wherein each longitudinal strut is connected to at least one of the plurality of stent elements.

5. The endoprosthesis of claim 1, wherein each longitudinal strut is disconnected from the plurality of stent elements.

6. The endoprosthesis of claim 1, wherein each longitudinal strut is oriented vertically between the pair of the plurality of stent elements.

7. The endoprosthesis of claim 1, wherein each longitudinal strut is oriented other than vertically between the pair of the plurality of stent elements.

8. The endoprosthesis of claim 7, wherein at least one of the longitudinal struts is a partial stent element.

9. The endoprosthesis of claim 1, wherein the plurality of stent elements and each longitudinal strut are external of the graft material.

10. The endoprosthesis of claim 1, wherein the plurality of stent elements and each longitudinal strut are internal relative to the graft material.

11. The endoprosthesis of claim 1, wherein the two legs are attached to one another.

12. The endoprosthesis of claim 11, further comprising sutures for attaching the two legs to one another.

13. The endoprosthesis of claim 1, wherein the two legs are of different dimensions.

14. The endoprosthesis of claim 1, wherein the two legs are of similar dimensions.

15. The endoprosthesis of claim 1, wherein the cranial and caudal sections are comprised of shape memory materials and laser cut from a common tube.

16. The endoprosthesis of claim 1, wherein the graft material is further comprised of a biocompatible material.

* * * * *